US00PP23552P2

(12) United States Plant Patent
Olesen

(10) Patent No.: US PP23,552 P2
(45) Date of Patent: Apr. 23, 2013

(54) ***ROSA* HYBRID VARIETY DENOMINATION 'POULPAL031'**

(50) Latin Name: ***Rosa* hybrid**
Varietal Denomination: Poulpal031

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/317,260

(22) Filed: Oct. 13, 2011

(51) Int. Cl.
*A01H 5/00* (2006.01)

(52) U.S. Cl. ..... Plt./135

(58) Field of Classification Search ..... Plt./135
See application file for complete search history.

*Primary Examiner* — Annette Para

(57) ABSTRACT

A new garden rose plant of the compact hybrid tea class which has abundant, orange blend flowers and attractive foliage. This new and distinct variety has shown to be uniform and stable in the resulting generations from asexual propagation.

4 Drawing Sheets

Botanical designation: *Rosa* hybrid.
Variety denomination: 'Poulpal031'.

SUMMARY OF THE INVENTION

The present invention constitutes a new and distinct variety of garden rose plant which originated from a controlled crossing between the female seed parent, an unnamed seedling, and the male pollen parent, an unnamed seedling.

The two parents were crossed during the summer of 2005 and the resulting seeds were planted in a controlled environment in Fredensborg, Denmark. The new variety, named 'Poulpal031', originated as a single seedling from the stated cross.

The new variety may be distinguished from its female seed parent primarily by the flower color. The seed parent has yellow flowers while the new variety has orange blend flowers.

The new variety may be distinguished from its male pollen parent primarily by flower color. The pollen parent has yellow flowers while the new variety has orange blend flowers.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal031' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poulpal031' was selected in the spring of 2006 by the inventor as a single plant from the progeny of the aforementioned hybridization.

Asexual reproduction of 'Poulpal031' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poulpal031' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpal031'. Specifically illustrated in the drawing are.

DETAILED DESCRIPTION OF THE VARIETY

Figure 1:
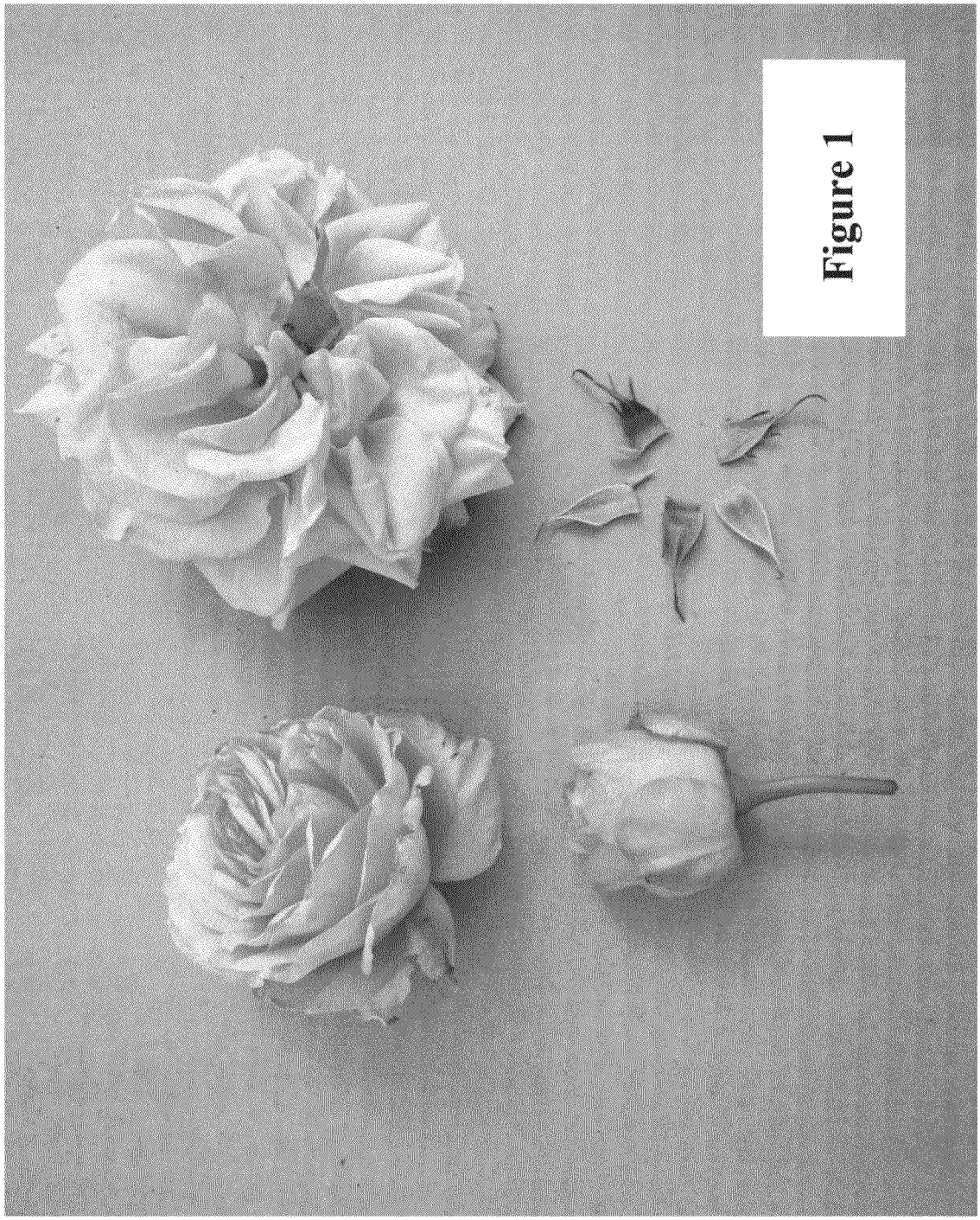
FIG. 1; Flowers at various stages of opening and sepals detached.
Figure 2:
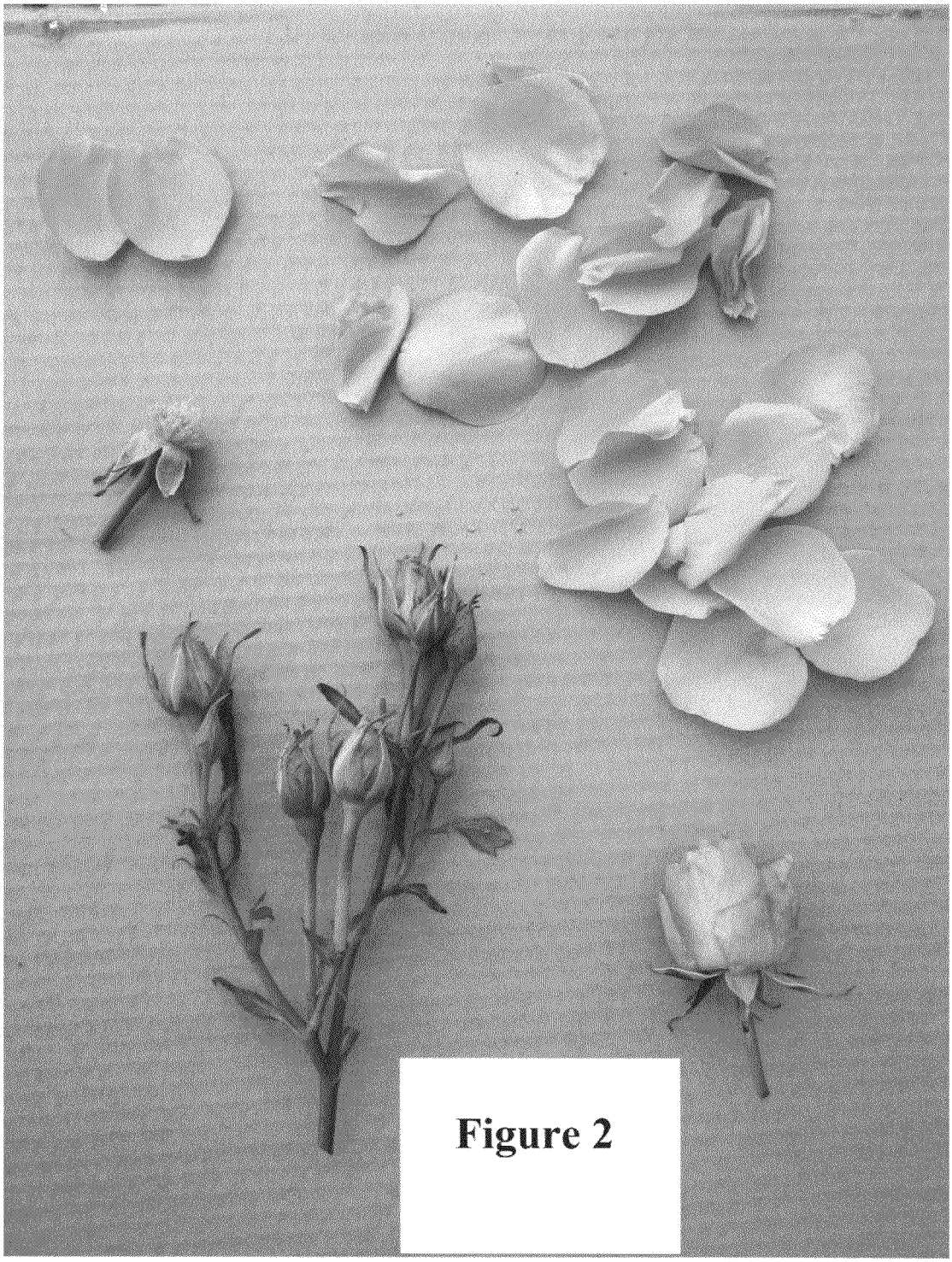
FIG. 2; Cluster of flowers on branch showing attachment of flower buds and flower petals detached.
Figure 3:
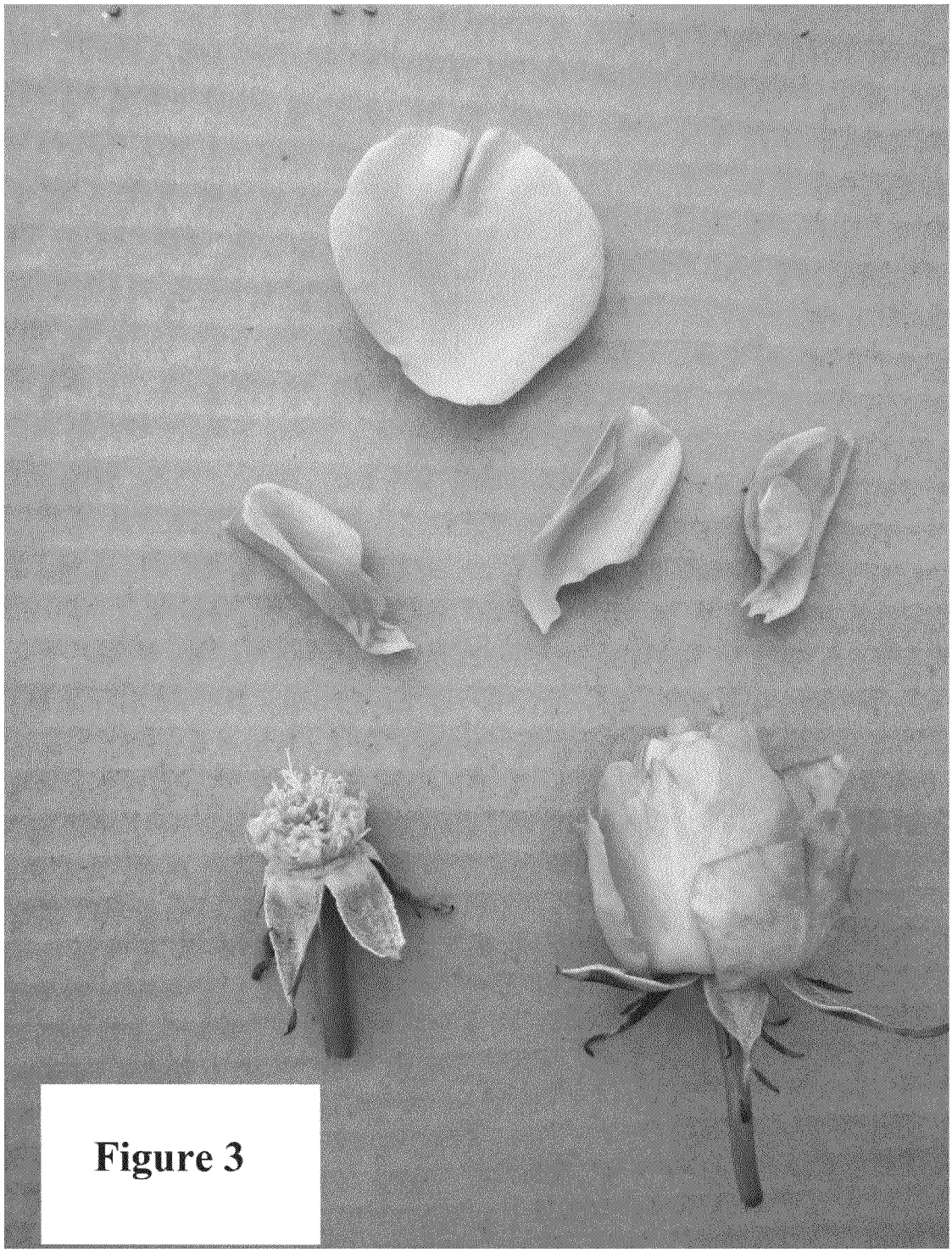
FIG. 3; Flower petals detached, reproductive flower parts, and flower side view upon opening.
Figure 4:
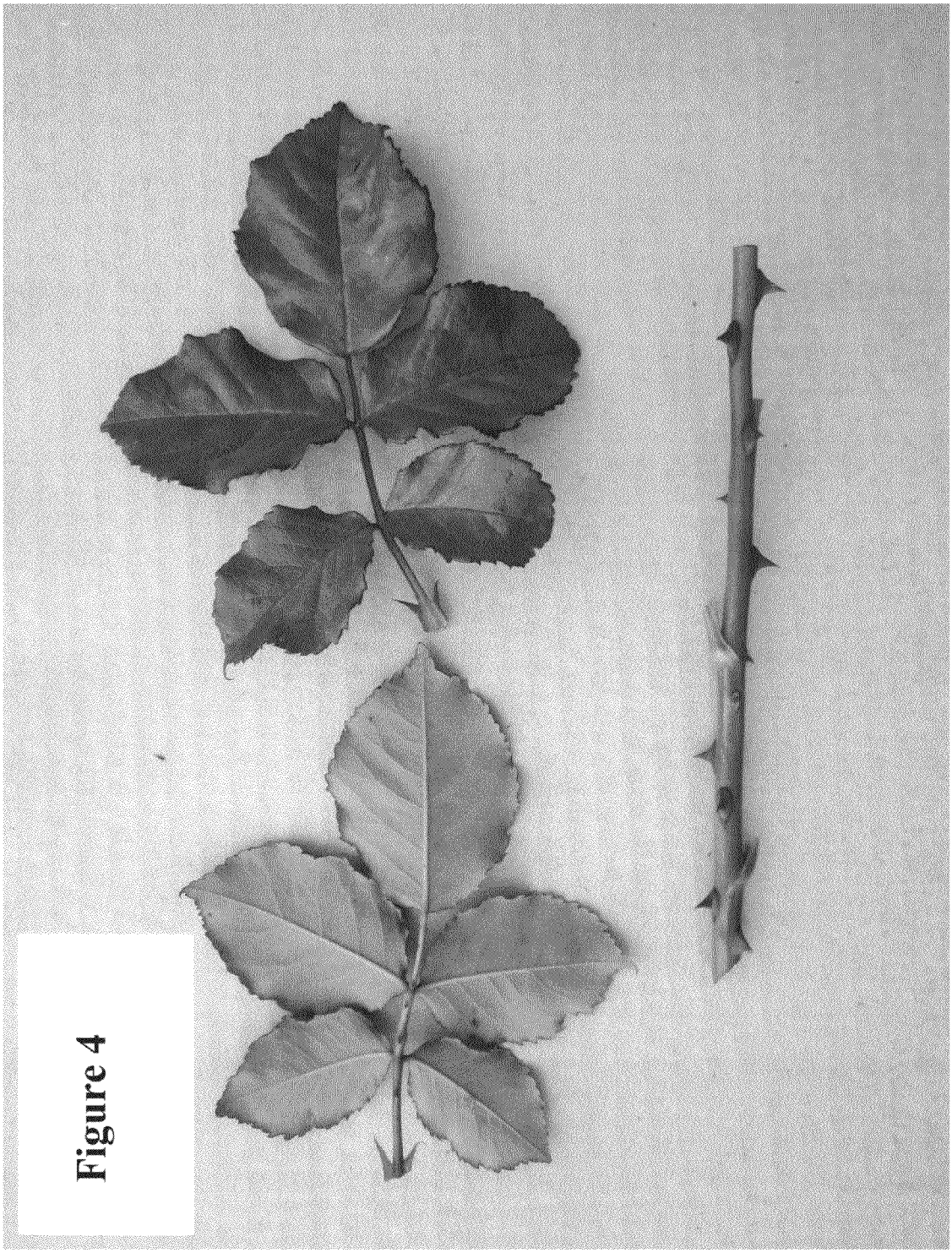
FIG. 4; Leaves and stem exhibiting thorns.

The following is a description of 'Poulpal031', as observed in its growth in in a field nursery in Benton County, Oreg. Observed plants are 21 months of age, and were grown from own root. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulpal031' in Chart 1.

CHART 1

| | 'Poulpal031' | 'Poulymp' |
|---|---|---|
| Petal Count | 60 to 70 petals | 25-30 petals |
| Flower Diameter | 90 to 110 mm | 60 to 70 mm |
| General Tonality of Flower Color | Orange Group 29C with intonations of Orange Group 24B | Yellow-Orange Group 20B, Orange Group 24C, and Yellow-Orange Group 21C |

FLOWER AND FLOWER BUD

Blooming habit: Recurrent.

Flower bud:

*Size*.—Upon opening, 30 mm in length from base of receptacle to end of bud. Bud diameter is 17 mm.

*Bud form*.—Ovoid.

*Bud color*.—As sepals unfold, petals are Orange-Red Group 35B with additional intonations of Red Group 53C and Yellow Group 12C.

*Sepal inner surface*.—Color: Yellow-Green Group 147D. Anthocyanin the color of Greyed-Purple Group 183C observed. Surface: Moderate pubescence.

*Sepal outer surface*.—Color: Yellow-Green Group 146D. Strong intonations of Greyed-Red Group 181A. Texture: Smooth.

*Sepal shape*.—Apex: Cirrhose. Base: Flat at union with receptacle.

*Sepal margin*.—Margins have medium foliaceous appendages on three of the five sepals.

*Sepal size*.—35 mm long by 10 mm wide.

*Receptacle*.—Texture: Smooth. Shape: Funnel shaped. Size: 5 mm (height) by 10 mm (wide). Color: Yellow-Green Group 144B with weak anthocyanic pigments the color of Greyed-Red Group 181A observed.

*Peduncle*.—Length: 4 to 10 cm. Diameter: 3 to 5 mm. Color: Yellow-Green Group 144C with strong anthocyanin Greyed-Purple Group 183C.

*Pedicel*.—Surface: Smooth. Few stipitate glands. Length: 25 to 30 mm. Diameter: 3 to 5 mm. Color: Yellow-Green Group 144C. Anthocyanic pigments the color of Greyed-Purple Group 183C observed. Strength: Strong.

Flower bud development: Flower buds are borne in clusters of 7 to 9 flower buds per stem, in panicle form.

Flower bloom:

*Fragrance*.—Moderate floral, candy scent.

*Duration*.—The blooms have a duration on the plant of approximately 15 days. Petals do not fall cleanly away from plant after flowers have fully matured.

*Size*.—Flower diameter is 90 to 110 mm when open. Flower depth is 45 mm.

*Flower shape*.—General shape is a hybrid tea, with a with a high pointed center which is tightly closed.

*Shape of flower, side view*.—Upon opening the upper portion is flat, while the lower portion is also flat.

Petalage: Under normal conditions, flowers have 60 to 70 petals total, about 20 of which are petaloids.

Petal color:

*Upon opening, outer petals*.—Upper surface: Orange Group 25C with margins the color of Orange-Red Group 31A and 31B. Lower surface: Orange-Red Group 35B with intonations of Orange-Red Group 29B.

*Upon opening, inner petals*.—Upper surface: Orange Group 25C with margins the color of Orange-Red Group 31A. Lower surface: Orange-Red Group 35A blended with Orange Group 29B.

*Basal petal spots, upon opening*.—Upper surface: Yellow Group 12A. Lower surface: Yellow Group 12B.

*After opening, outer petals*.—Upper surface: Blend of Orange Group 27C and 24C. Lower surface: Orange Group 24D with marginal intonations of Red Group 37D.

*After opening, inner petals*.—Upper surface: Yellow-Orange Group 22B. Lower surface: Orange Group 32C blended with Red Group 37C at margins.

*Basal petal spots, after opening*.—Upper surface: Yellow Group 12B. Lower surface: Yellow Group 12C.

General tonality: On open flower Orange Group 29C with intonations of Orange Group 24B. After 10 days general tonality is Orange Group 27A.

Petals:

*Petal reflex*.—Somewhat reflexed.

*Margin*.—Entire and uniform. Occasionally a slight point at the center of the margin. Weak undulations of margin observed.

*Shape*.—Generally rounded or broadly elliptic. Apex shape: Rounded. Base shape: Both acute and rounded.

*Size*.—50 mm (l)×45 mm (w). Inner petals are smaller, 35 mm (l)×30 mm (w).

*Texture*.—Smooth.

*Thickness*.—Average.

Petaloids:

*Quantity*.—Average 20.

*Shape*.—Elliptic.

*Color*.—Orange Group 25C, margins Orange-Red Group 31A, with Yellow Group 12A petal spot on the upper portion. Lower portion is Orange-Red Group 35A blended with Orange Group 29B, and a petal spot Yellow Group 12B.

*Size*.—20 mm wide by 25 mm long.

Reproductive organs:

*Pollen*.—None observed.

*Anthers*.—Size: 2 mm in length. Color: Yellow Group 11A. Quantity: 120 on average.

*Filaments*.—Color: Yellow Group 12B. Length: 5 mm.

*Pistils*.—Length: 7 mm. Quantity: About 75.

*Stigmas*.—Superior in location relative to the length of the filaments and the height of the anthers. Color: Yellow Group 8C.

*Styles*.—Color: Orange-Red Group 27D.

*Hips*.—None observed.

PLANT

Plant growth: Upright. As a field grown plant on its own roots the average height of the plant is 60 cm and the average width is 60 cm.

Stems:

*Color*.—Mature growth: Yellow-Green Group 144B and Greyed-Orange Group 174A. Juvenile growth: Yellow-Green Group 144B with light intonations of Greyed-Orange Group 174A.

*Length*.—On average, canes are 40 cm from the base of the plant to the flowering portion.

*Diameter*.—6 to 8 mm.

*Internodes*.—On mature canes, there is an average distance of 8 cm mm between nodes.

*Surface texture*.—Young wood: Smooth. Older wood: Smooth.

Prickles:

*Incidence*.—5 to 6 prickles per 10 cm of stem.

*Size*.—Average length of prickles on mature stems is 9 mm.

*Shape*.—Linear on the upper side, concave on the lower side.

*Color*.—Juvenile prickles: Greyed-Red Group 182A. Mature prickles: Greyed-Red Group 182A and Greyed-Yellow Group 162B.

Plant foliage: Normal number of leaflets leaves in middle of the stem: 5 leaflets.

*Compound leaf*.—150 mm (l)×120 (w).

*Quantity*.—2 leaves per 10 cm of stem on average.

*Color of mature foliage*.—Upper side: Yellow-Green Group 146A. Lower side: Yellow-Green Group 147C.

*Color of juvenile foliage*.—Upper side: Yellow-Green Group 146A. Lower side: Yellow-Green Group 147C.

Plant leaves and leaflets:

*Stipules*.—Size: 7 mm in length. Quantity: 2 per compound leaf. Shape: Linear, slightly broad based with outward extending apices. Margins: Finely serrated with few stipitate glands. Color: Yellow-Green Group 144B.

*Petiole*.—Length: 30 mm. Diameter: 2 mm.

*Upper surface*.—Color: Greyed-Red Group 181B.

*Lower surface*.—Color: Yellow-Green Group N144C with anthocyanin Greyed-Red Group 181C.

*Rachis*.—Length: 35 mm. Upper surface: Color: Greyed-Red Group 181B.

*Lower surface*.—Color: Yellow-Green Group N144C with anthocyanin Greyed-Red Group 181C.

*Leaflet*.—Margin: Doubly serrate. Size: Terminal leaflets on normal leaves are 65 to 70 mm in length by 50 to 55 mm wide. Shape: Generally ovate. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery and downy mildew, rust, and Botrytis under normal growing conditions in Benton County, Oreg. Average resistance to black spot.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the compact hybrid tea rose class named ‘Poulpal031’, substantially as illustrated and described herein, due to its abundant orange blend flowers, disease resistance, and extended period of bloom.

* * * * *